United States Patent [19]

McDaniel

[11] Patent Number: 5,423,845
[45] Date of Patent: Jun. 13, 1995

[54] SURGICAL SAW BLADE

[75] Inventor: John M. McDaniel, Bloomington, Ind.

[73] Assignee: Biomet, Inc., Warsaw, Ind.

[21] Appl. No.: 212,393

[22] Filed: Mar. 10, 1994

Related U.S. Application Data

[63] Continuation of Ser. No. 902,393, Jun. 18, 1992, abandoned, which is a continuation of Ser. No. 665,992, Mar. 7, 1991, abandoned.

[51] Int. Cl.$^6$ ............................................. A61B 17/14
[52] U.S. Cl. .................................... 606/176; 30/355; 83/835; 83/848; 606/178
[58] Field of Search ................ 606/176, 177, 82, 178; 30/355; 83/835, 846, 848, 851

[56] References Cited

U.S. PATENT DOCUMENTS

| | | | |
|---|---|---|---|
| 108,040 | 10/1870 | Milliman | 83/848 |
| 1,246,905 | 11/1917 | Garlock et al. | 83/846 |
| 2,072,624 | 3/1937 | Owen | 83/848 |
| 2,351,737 | 6/1944 | Blum | 83/848 |
| 3,905,374 | 9/1975 | Winter | 606/178 |
| 4,031,789 | 6/1977 | Soodalter | 83/835 X |
| 4,461,198 | 7/1984 | Grassmann | 83/835 |
| 4,492,141 | 1/1985 | Takeuchi | 30/355 X |
| 4,802,396 | 2/1989 | Kuklinski | 83/835 X |

FOREIGN PATENT DOCUMENTS 1165380  7/1985  U.S.S.R. ............... 606/176

OTHER PUBLICATIONS

"Why Is Pull Stroke Better?", Takagi Tools, Inc. Brochure (Undated).

Komet Medical; Brochure entitled "The Search for the Next Dimension in Surgical Technology".

Primary Examiner—Michael H. Thaler
Attorney, Agent, or Firm—Barnes & Thornburg

[57] ABSTRACT

A blade for a surgical saw has an elongate body with distal and proximal ends, and a plurality of teeth formed on an outwardly facing edge surface of the distal end. The spaces between adjacent teeth are defined by surfaces which lie in planes which are non-perpendicular to the substantially flat surfaces which define the body of the blade. These non-perpendicular surfaces guide cuttings generated by the teeth laterally toward the flat surfaces of the blade and outwardly toward the proximal end of the blade as the blade advances in a cut. Each of the teeth formed on the edge of the blade has a pointed form. Approximately half of the teeth lie in a row in which the respective points lie in a first cutting plane which extends in parallel with, and lies adjacent a first side of, a plane which extends longitudinally through the center of the blade body. The remaining teeth have points which lie in a second row in a second cutting plane which extends in parallel with, and lies adjacent a second side of, the plane which extends longitudinally through the blade body. The teeth have triangular cross-sections and are formed on alternatingly intersecting angled surfaces formed on the distal edge. The base of each tooth lies in the same plane as the surface upon which the tooth is formed. Each tooth has two side surfaces extending upwardly from the base and intersecting above the base to form a point. In the embodiment illustrated, the side surfaces are shaped as parallelograms and share a common side so as to form a knife-edge cutting surface which extends from the point backwardly toward the proximal end of the blade.

27 Claims, 1 Drawing Sheet

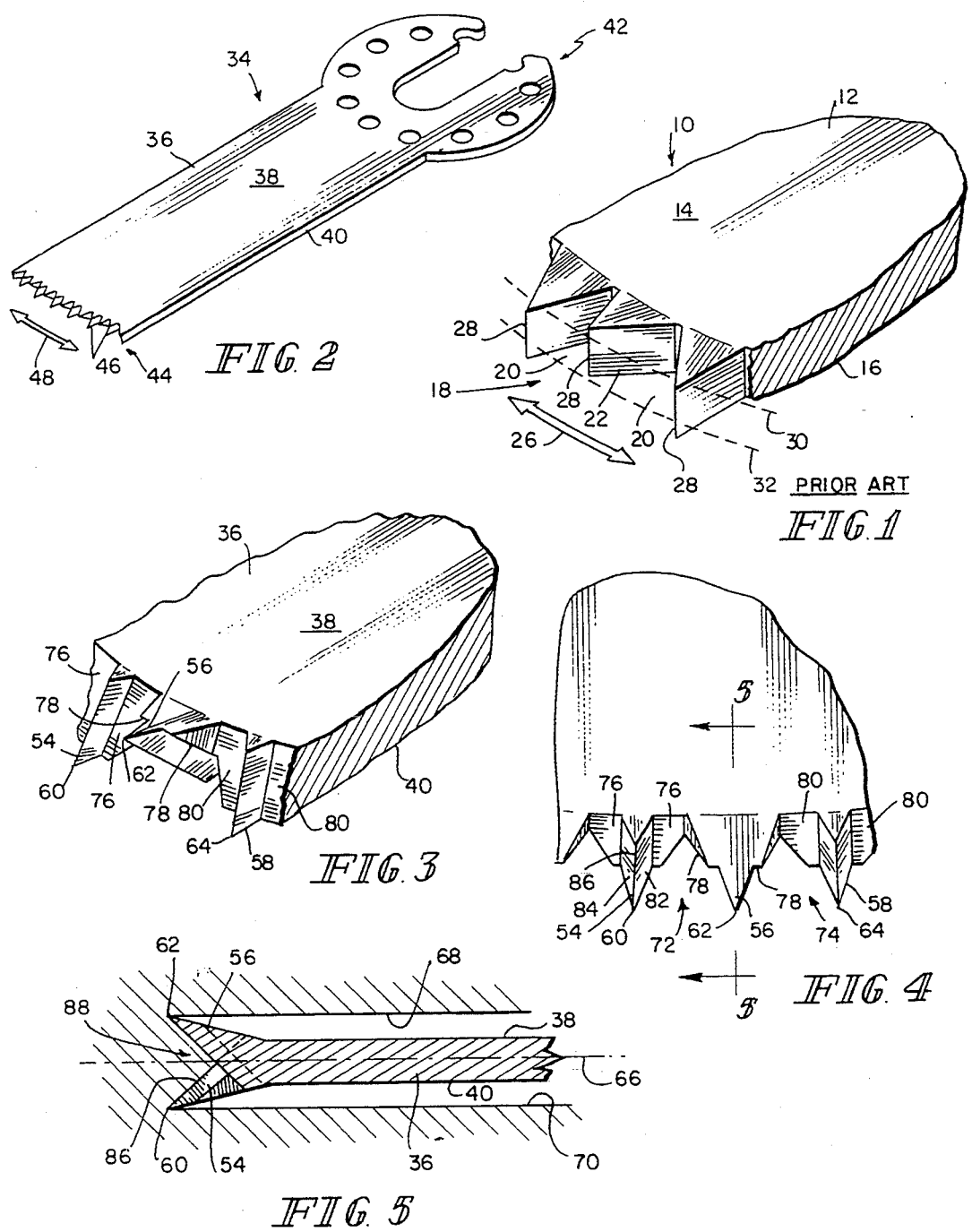

SURGICAL SAW BLADE

This is a Continuation of Application Ser. No. 07/902,393, filed Jun. 18, 1992, now abandoned, which is a continuation of Application Ser. No. 07/665,992, filed Mar. 7, 1991, now abandoned.

BACKGROUND AND SUMMARY OF THE INVENTION

This invention relates generally to saw blades and, more specifically, to an improved blade for a surgical saw.

A conventional blade for a surgical saw has a relatively flat, elongated body which is attached at one end to a powered drive source. A row of teeth is typically formed on an outwardly facing edge surface of the end of the blade opposite the drive source. The drive source imparts a reciprocating motion to the blade which is used to effect the cutting of relatively hard body tissues. The angular excursion of the reciprocating blade is severely limited to prevent the accidental cutting of soft tissues which tend to vibrate or move with the blade upon contact with the saw blade teeth.

A conventional saw tooth pattern typically incorporates a gullet (i.e., the space between adjacent teeth) which is defined by surfaces which lie in planes generally perpendicular to the flat surfaces of the blade. This pattern is satisfactory in applications where the teeth exit the cut and deposit cuttings, stored in gullets, outside the cut. In the case of a surgical saw application, the teeth typically do not leave the cut and, accordingly, cuttings tend to build up in the gullets and retard cutting. The substantially perpendicular surfaces which define the gullets in a conventional blade effectively trap the cuttings between the sharp surfaces of the teeth.

An object of the present invention is to provide an improved tooth design for a surgical saw which overcomes problems associated with conventional saw tooth designs.

Another object of the present invention is to provide an improved tooth design for a surgical saw in which relatively large spaces are provided between adjacent teeth, and in which these spaces are defined by surfaces which lie in planes which are non-perpendicular to the flat surfaces of the blade.

These and other objects of the invention are attained in a blade for a surgical saw which comprises an elongate body having first and second substantially flat surfaces, and having a proximal end and a distal end. A plurality of teeth are formed on an outwardly facing edge surface of the distal end of the blade. The spaces between adjacent teeth are defined by surfaces which lie in planes which are non-perpendicular to the first and second substantially flat surfaces whereby the cuttings generated by the teeth are guided laterally toward the flat surfaces of the blade and outwardly toward the proximal end of the blade as the blade advances in a cut.

The plurality of teeth formed on the outwardly facing edge surface of the end of the blade preferably include a first set of teeth spaced apart in a first row and a second set of teeth spaced apart in a second row. Each tooth of the first set has a point which lies in a first cutting plane which extends in parallel with, and lies adjacent a first side of, a plane which extends longitudinally through the center of the body. Each tooth of the second set has a point which lies in a second cutting plane which extends in parallel with, and lies adjacent a second side of, the plane which extends longitudinally through the center of the body. The plurality of teeth are disposed in alternating relation such that each tooth in the first set is disposed between two teeth of the second set, and vice versa.

In one embodiment of the blade, at least one of the surfaces which define the spaces between adjacent teeth intersects the longitudinal plane which extends through the center of the blade, and the substantially parallel flat surfaces of the blade, at an angle of approximately 45°. In another embodiment, each space between adjacent teeth is defined by at least two surfaces which lie in such planes, and which intersect each other at an angle of approximately 90°.

In one embodiment of the invention, the outwardly facing edge of the blade comprises a plurality of alternating surfaces which lie in alternately intersecting planes. These planes intersect the longitudinal plane which extends through the center of the blade at substantially equal acute angles. Each of the alternating teeth of the blade is formed on a respective one of these alternating surfaces. Each of these teeth have a triangular cross-section, and comprises a base, which lies in the same plane as the surface upon which the tooth is formed, and two side surfaces extending upwardly from the base and intersecting above the base to form the point of the tooth. The base of the triangular tooth has a width which only partly covers the coplanar surface upon which the tooth is formed. The portions of the surface on either side of the base of the tooth form "back" surfaces of the space between adjacent teeth (i.e., the gullet). Those surfaces are aligned to "face" the direction of the cut, but are angled so as to guide cuttings produced by the blade outwardly and backwardly toward the proximal end of the blade. Each of the side surfaces of the tooth is shaped as a parallelogram which shares a common side to form a knife-like cutting edge extending from the point backwardly toward the proximal end of the blade.

In one embodiment of the blade, the first and second cutting planes are substantially parallel to, and are spaced outwardly from, the first and second substantially flat surfaces of the blade. This embodiment increases the width of the kerf to provide more room for cuttings to be deposited between the body of the blade and the cut surfaces.

Other objects, advantages and novel features of the present invention will become apparent from the following detailed description of the invention when considered in conjunction with the accompanying drawings.

BRIEF DESCRIPTION OF THE DRAWINGS

FIG. 1 shows a perspective view of a prior art tooth design.

FIG. 2 shows a perspective view of a surgical saw blade constructed in accordance with the present invention.

FIGS. 3 and 4 show a perspective view and a frontal view, respectively, of a portion of the tooth pattern of the saw blade of FIG. 2, enlarged to show the improved tooth pattern in detail.

FIG. 5 shows a cross-section through a portion of the blade taken along line 5—5 of FIG. 4 as the blade advances in a cut.

DETAILED DESCRIPTION OF THE DRAWINGS

FIG. 1 shows an enlarged view of a portion of a conventional blade 10 for a surgical saw. Blade 10 has a relatively flat elongated body 12 having relatively flat opposing surfaces 14 and 16. A row of teeth 18 is formed on an outwardly facing edge surface of body 12. The space 20 between adjacent teeth, which is commonly referred to as a gullet, is defined by the facing rectangular surfaces of adjacent teeth (e.g., these surfaces lie in planes which are substantially perpendicular to surfaces 14 and 16 of blade 10.

In operation, blade 10 reciprocates, as generally illustrated by arrow 26, so that the cutting edges 28 of teeth 18 can cut into bone or other relatively hard tissue. The cuttings generated collect in the spaces 20 between adjacent teeth. However, since these spaces are defined by surfaces which are generally perpendicular to surfaces 14 and 16 of body 12, the cuttings tend to become trapped causing a build-up in spaces 20, and subsequent retardation of cutting action.

Note that alternating ones of the plurality of teeth 18 are slightly offset above and below (as shown in FIG. 1), arcuate planes 30 and 32. This offset produces a relatively wide kerf, or width of cut, which is wider than the thickness of elongate body 12. This additional space should, and does, provide some room for cuttings generated by the plurality of teeth 18. However, the generally perpendicular surfaces (such as surface 22) still tend to trap cuttings within the gullets and, in any event, do not promote movement of the cuttings into this additional space.

FIG. 2 shows a perspective view of an improved blade 34 which is constructed in accordance with the principles of the present invention. Blade 34 has an elongate body 36 which, in turn, has first and second substantially flat surfaces 38 and 40, respectively. Blade 34 has a proximal end 42 and a distal end 44. A plurality of teeth 46 are formed on an outwardly facing edge surface of distal end 44. Proximal end 42 of blade 34 is adapted to be connected to a drive source which imparts a reciprocating motion to blade 34, as indicated by arrow 48, to effect the cutting of relatively hard body tissues.

FIGS. 3 and 4 show perspective and frontal views, respectively, of an enlarged portion of blade 34. Three of the plurality of teeth formed on the distal edge surface of blade 34 are shown in FIGS. 3 and 4. These teeth are numbered 54, 56 and 58, respectively. Teeth 54 and 58 are part of a first set of teeth which are spaced apart in the first row along the edge of the blade, while tooth 56 is part of a second set of teeth also spaced apart in a second row along the blade edge. Each of these teeth has a sharp point which results from the structure of the blade as described in detail below. These points are numbered 60, 62 and 64, respectively, in FIGS. 3 and 4. Points 60 and 64 lie in a first cutting plane which extends in parallel with, and lies adjacent a first side of, a plane which extends longitudinally through the center of elongate body 36 of blade 34. This is best illustrated in FIG. 5 which is a cross-sectional view through tooth 56. In this view, the plane which extends longitudinally through the center of body 36 is indicated by a dashed line numbered 66. Point 62 of tooth 56 lies in a first cutting plane 68 which extends in parallel with, and lies adjacent a first side of, plane 66. Point 60 of tooth 54 lies in a second cutting plane 70 which also extends in parallel with, and lies adjacent a second side of, plane 66. This arrangement of alternating teeth in two cutting planes is similar to tooth patterns used on saws in certain woodworking applications. However, the manner and environment in which the saw of the present invention is used, particularly in regard to such aspects as blade excursion angle and the handling of cuttings, differ markedly from that of the woodworking environment. As shown in FIG. 5, planes 68 and 70 are also spaced apart from sides 38 and 40, respectively. The spaces between side 38 and plane 68, on the one hand, and side 40 in plane 70 on the other hand, receive cuttings generated as the blade advances in the cut.

Referring again to FIGS. 3 and 4, it can be seen that teeth 54 and 58, which lie in the first row, are arranged in alternating relation with the teeth in the second row (e.g., tooth 56) such that the respective points of these teeth are alternatingly disposed in planes 68 and 70, respectively. The teeth are triangular in shape (as described in more detail below) and are separated by at least surfaces 76 and 78. This arrangement produces comparatively large spaces (i.e., gullets) between adjacent teeth which are best illustrated in FIG. 4 and are numbered 72 and 74, respectively. Spaces 72 and 74 are defined by surfaces which lie in planes which are non-perpendicular to the relatively flat surfaces 38 and 40 of blade 34. This arrangement guides cuttings generated by the teeth laterally toward the flat surfaces of blade 34 and outwardly toward the proximal end of the blade and into the spaces between surfaces 38 and 40 and cutting planes 68 and 70, respectively, as the blade advances in a cut. Cuttings can also escape into the porosity of the material (e.g., cancellous bone) being cut.

One manner in which the improved tooth pattern of the present invention may be described is in terms of alternating surfaces 76, 78 and 80, respectively, formed on the outwardly facing distal edge of body 36. These surfaces are preferably substantially flat surfaces which lie in planes which are oblique to the direction of travel of the blade. Stated differently, these surfaces are angled, relative to longitudinal plane 66, so as to guide cuttings generated by the teeth laterally and outwardly away from the cutting teeth.

Teeth 54, 56 and 58 can be described as having triangular cross-sections which comprise, in the case of tooth 54, a base which lies on surface 76, and two parallelogram-shaped side surfaces 82 and 84 which extend upwardly from the base and intersect to form point 60. Surfaces 82 and 84 also share a common side 86 which forms the knife-like cutting edge which extends from point 60 backwardly toward the proximal end 42 of blade 34. As previously noted, the base of each of the triangular teeth only partly covers the surface upon which the tooth is formed. Thus, space 72 is defined by surfaces 76, 78, 82 and one of the parallelogram-shaped sides of tooth 56 (not shown). Surfaces 76 and 78 are aligned to "face" the direction of the cut, but lie in planes which are oblique to this direction. In the particular embodiment shown in the drawings, these surfaces are parallel to the knife-like cutting edge on the adjacent teeth. By virtue of their angled relationship to the direction of blade advance into the cut, these surfaces serve as a guide to direct cuttings away from the distal end of the blade.

To summarize, this arrangement produces at least two benefits when compared to prior art saw-tooth patterns. First, the volume of space 72 is larger than the volume of the spaces or gullets of prior art tooth patterns. Secondly, space 72 is defined by surfaces which lie in planes which are non-perpendicular to the flat surfaces 38 and 40 of blade 34, and to plane 66 which extends longitudinally through the center of blade 34. These non-perpendicular surfaces tend to guide cuttings produced by the teeth backwardly away from the cutting area and, do not trap the cuttings between the teeth in the same manner as occurs in prior art, tooth patterns in which gullets are defined by surfaces which are substantially parallel to blade surfaces.

An additional aspect of the present design is also apparent in FIG. 5. The teeth of the blade which have points which lie in a row with point 62 of tooth 56 penetrate the material along cutting plane 68, while the teeth having points which lie in a row with point 60 of tooth 54 penetrate the material along cutting plane 70. This dual penetration leaves a "cantilever" of material, indicated generally in FIG. 5 by reference numeral 88 which may be more easily dislodged by the cutting surfaces of the teeth. This arrangement is very similar to teeth patterns used in other applications (such as woodworking), but is felt by the present inventor to be particularly effective in combination with the non-perpendicular surfaces which guide cuttings away from the teeth, in the somewhat unique environment of surgical saws.

In the embodiment of the blade shown in FIGS. 2–5, surfaces 76, 78 and 80 lie in planes which intersect longitudinal planes 66 at respective angles of approximately 45°. As noted, these surfaces alternate so that, for example, surfaces 76 and 78 also intersect each other at an angle of approximately 90°. These angles, as well as the angles which define the triangular cross-section of the teeth, may be varied to increase or decrease the volume of the spaces between alternating teeth (e.g., 72 and 74) as desired. Indeed, increasing the angle to, for instance, 60°, may enhance the chip clearing capabilities of the blade. However, this arrangement also changes the geometry of the individual teeth in ways which may reduce cutting effectiveness or blade life. At present, the inventor considers the 45° angles illustrated to be a desirable compromise among these competing design considerations.

From the preceding description of the preferred embodiments, it is evident that the objects of the invention are attained. Although the invention has been described and illustrated in detail, it is to be clearly understood that the same is intended by way of illustration and example only and is not to be taken by way of limitation. The spirit and scope of the invention are to be limited only by the terms of the appended claims.

What is claimed is:

1. A blade for a surgical saw, comprising an elongate body having first and second substantially flat surfaces, and having a proximal end and a distal end and a plurality of teeth formed on an outwardly facing edge surface of said distal end, each of said teeth having a base and at least two surfaces which intersect to define a cutting edge, and wherein the bases of adjacent teeth are separated by a space, each of the spaces between the bases of adjacent teeth being defined by at least two, substantially flat intersecting surfaces which lie in intersecting planes which are non-perpendicular to the first and second substantially flat surfaces, wherein each of said intersecting surfaces defining said spaces is angled relative to each of said surfaces which intersect to define the cutting edges wherein one of said intersecting surfaces defining said space intersects said first flat surface at an angle so as to guide cuttings generated by the adjacent teeth laterally toward said first surface, and wherein the other of said intersecting surfaces defining said space intersects said second flat surface at an angle so as to guide cuttings laterally toward said second surface, as the blade advances in a cut.

2. A blade for a surgical saw according to claim 1, wherein said plurality of teeth comprise a first set of teeth spaced apart in a first row and a second set of teeth spaced apart in a second row, each tooth of said first set having a point which lies in a first cutting plane which extends in parallel with, and lies adjacent a first side of, a plane which extends longitudinally through the center of the body, each tooth of said second set having a point which lies in a second cutting plane which extends in parallel with, and lies adjacent a second side of, the plane which extends longitudinally through the center of the body, said plurality of teeth being disposed in alternating relation such that each tooth in the first set is disposed between two teeth of the second set, and vice versa.

3. A blade for a surgical saw according to claim 2, wherein the first and second cutting planes are substantially parallel to, and are spaced outwardly from, the first and second substantially flat surfaces of the blade.

4. A blade for a surgical saw according to claim 1, wherein at least one of said surfaces which define the spaces between adjacent teeth intersects a longitudinal plane which extends through the center of the blade at an angle of approximately 45°.

5. A blade for a surgical saw according to claim 1, wherein said at least two intersecting surfaces lie in planes which intersect a longitudinal plane which extends through the center of the blade at angles of approximately 45°, and intersect each other at an angle of approximately 90°.

6. A blade for a surgical saw according to claim 1, wherein said intersecting surfaces which lie in intersecting planes intersect at substantially equal acute angles.

7. A blade for a surgical saw according to claim 6, wherein each of said teeth has a triangular cross-section and wherein the base lies in the same plane as the adjacent surface which defines a portion of the adjacent space.

8. A blade for a surgical saw according to claim 7, wherein each of the side surfaces of the tooth is shaped as a parallelogram, and wherein the parallelogram-shaped surfaces share a common side so as to form the cutting edge extending from the point backwardly toward the proximal end of the blade.

9. A blade for a surgical saw according to claim 8, wherein at least one of said substantially flat intersecting surfaces is substantially parallel to said cutting edge.

10. A blade for a surgical saw, comprising an elongate body having first and second substantially flat surfaces, and having a proximal end and a distal end and a plurality of teeth formed on an outwardly facing edge surface of said distal end, wherein said plurality of teeth comprise a first set of teeth spaced apart in a first row and a second set of teeth spaced apart in a second row, each tooth of said first set having a point which lies in a first cutting plane which extends in parallel with and lies adjacent a first side of a plane which extends longitudinally through the center of the body, each tooth of said second set having a point which lies in a second cutting plane which extends in parallel with and lies adjacent a second side of the plane which extends longitudinally through the center of the body, said plurality of teeth being disposed in alternating relation such that each tooth in the first set is disposed between two teeth of the second set, and vice versa, and wherein said outwardly facing edge comprises a plurality of alternating, substantially flat surfaces which lie in alternately intersecting planes, which planes also intersect a longitudinal plane which extends through the center of the blade at substantially equal acute angles, as measured from a point on said plane which extends longitudinally through the center of the body, and wherein each of said plurality of teeth comprises at least two surfaces which intersect to define a cutting edge, and wherein each of said plurality of teeth is formed on a respective one of said alternating surfaces, and wherein adjacent teeth are spaced apart on said alternating surfaces such that each space is defined by intersecting portions of adjacent alternating surfaces, and wherein each of said alternating surfaces is angled relative to each of said surfaces which intersect to define the cutting edges.

11. A blade for a surgical saw according to claim 10, wherein each of said teeth has a triangular cross-section and comprises a base, which lies in the same plane as the surface upon which the tooth is formed, and two side surfaces extending upwardly from the base and intersecting above the base to form the point.

12. A blade for a surgical saw according to claim 11, wherein each of the side surfaces of the tooth is shaped as a parallelogram, and wherein the parallelogram-shaped surfaces share a common side so as to form a knife-like cutting edge extending from the point backwardly toward the proximal end of the blade.

13. A blade for a surgical saw according to claim 12, wherein at least one of said plurality or alternating surfaces is substantially parallel to the knife-like cutting edge.

14. A blade for a surgical saw according to claim 10, wherein the surfaces which define the spaces between adjacent teeth lie in planes which are non-perpendicular to the first and second substantially flat surfaces, whereby said non-perpendicular surfaces guide cuttings generated by the teeth laterally toward the flat surfaces of the blade and outwardly toward the proximal end of the blade as the blade advances in a cut.

15. A blade for a surgical saw according to claim 14, wherein at least one of said surfaces which define the spaces between adjacent teeth intersects the longitudinal plane which extends through the center of the blade at an angle of approximately 45°.

16. A blade for a surgical saw according to claim 14, wherein each space between adjacent teeth is defined by at least two surfaces which lie in planes which intersect the longitudinal plane which extends through the center of the blade at angles of approximately 45°, and intersect each other at an angle of approximately 90°.

17. A blade for a surgical saw, comprising an elongate body having first and second substantially flat surfaces, and having a proximal end and a distal end and a plurality of teeth formed on an outwardly facing edge surface of said distal end, each of said teeth having a triangular cross-section, as viewed from a plane which extends longitudinally through the body of the blade, said cross-section having a base and a height, and each of said teeth having a length as measured transversely through said plane, said length being substantially greater than said height and base, and wherein the bases of adjacent teeth are separated by a space defined by at least two intersecting surfaces which are non-perpendicular to the first and second substantially flat surfaces, wherein one of said intersecting surfaces defining said space intersects said first flat surface at an angle so as to guide cuttings generated by the adjacent teeth laterally toward said first surface, and wherein the other of said intersecting surfaces defining said space intersects said second flat surface at an angle so as to guide cuttings laterally toward said second surface, as the blade advances in a cut and wherein each of said teeth comprises a pair of side surfaces extending upwardly from said base and intersecting along a common side to form a cutting edge and wherein each of said intersecting surfaces defining said spaces is angled relative to each of said side surfaces.

18. A blade for a surgical saw according to claim 17, wherein said side surfaces are shaped as parallelograms, and wherein adjacent corners of said pair of surfaces intersect to form a point at a distal end of each tooth.

19. A blade for a surgical saw according to claim 17, wherein the intersecting surfaces which define the spaces between the bases of adjacent teeth are substantially flat, planar surfaces.

20. A blade for a surgical saw according to claim 19, wherein at least one of said surfaces which define the spaces between adjacent teeth intersects the longitudinal plane which extends through the center of the blade at an angle of approximately 45°.

21. A blade for a surgical saw according to claim 19, wherein said at least two intersecting surfaces lie in planes which intersect the longitudinal plane which extends through the center of the blade at angles of approximately 45°, and intersect each other at an angle of approximately 90°.

22. A blade for a surgical saw according to claim 17, wherein said cutting edge extends in substantially parallel relation to at least one of said intersecting surfaces which define the space between adjacent teeth.

23. A blade for a surgical saw, comprising an elongate body having first and second substantially flat surfaces, and having a proximal end and a distal end, a plurality of alternating surfaces formed on an outwardly facing edge surface of said distal end, said surfaces alternatingly arranged to intersect respective ones of said first and second substantially flat surfaces at first and second angles, respectively, and a plurality of teeth formed, respectively, on said alternating, intersecting surfaces, each tooth having a narrow base disposed in a central region of the respective surface so as to leave substantial portions of said surface exposed on either side of said base, wherein said exposed portions of adjacent surfaces guide cuttings generated by adjacent teeth laterally toward said first and second surfaces, respectively, and away from the distal end of the blade as the blade advances in a cut.

24. A blade for a surgical saw according to claim 23, wherein each of said teeth comprises a pair of side surfaces extending upwardly from said base and intersecting along a common side to form a cutting edge.

25. A blade for a surgical saw according to claim 24, wherein said side surfaces are shaped as parallelograms, and wherein adjacent corners of said pair of surfaces intersect to form a point at a distal end of each tooth.

26. A blade for a surgical saw according to claim 23, wherein said actuating surfaces intersect said first and second substantially flat surfaces at approximately 45°.

27. A blade for a surgical saw according to claim 23, wherein each of said teeth are triangular in cross-section, as viewed from a longitudinal plane extending through the center of the blade, and wherein a length of each tooth as measured transversely to said longitudinal plane is substantially greater than a width of said base.

* * * * *